United States Patent [19]

Fischell et al.

[11] Patent Number: 4,661,097
[45] Date of Patent: Apr. 28, 1987

[54] METHOD FOR CLEARING A GAS BUBBLE FROM A POSITIVE DISPLACEMENT PUMP CONTAINED WITHIN A FLUID DISPENSING SYSTEM

[75] Inventors: Robert E. Fischell, Silver Spring; Albert C. Sadilek, Elkridge, both of Md.; William Swift, Fountain Valley, Calif.

[73] Assignee: The Johns Hopkins University, Baltimore, Md.

[21] Appl. No.: 616,255

[22] Filed: Jun. 1, 1984

[51] Int. Cl.⁴ ............................................. A61M 1/00
[52] U.S. Cl. ................................................... 604/123
[58] Field of Search ........ 604/122, 123, 126, 151-155, 604/27, 35, 85-88; 129/DIG. 12

[56] References Cited

U.S. PATENT DOCUMENTS

| | | | |
|---|---|---|---|
| 4,188,948 | 2/1980 | Swinton ............................... | 604/126 |
| 4,217,894 | 8/1980 | Franetzki et al. .................... | 604/131 |
| 4,221,219 | 9/1980 | Tucker ................................. | 604/141 |
| 4,265,241 | 5/1981 | Portner et al. ...................... | 128/D12 |
| 4,360,019 | 10/1982 | Portner et al. ...................... | 604/151 |
| 4,465,470 | 8/1984 | Kelman .............................. | 604/27 |
| 4,511,355 | 4/1985 | Franetzki et al. ................... | 604/891 |

*Primary Examiner*—John D. Yasko
*Attorney, Agent, or Firm*—Robert E. Archibald; Howard W. Califano

[57] ABSTRACT

A method and apparatus for removing gas bubbles from the fluid handling system of a medication infusion system is disclosed. Specifically, the invention discloses a method for removing fluid and/or gas bubbles from fluid reservoir and pumping chamber. The present invention utilizes a fluid pump of a single valve positive displacement design with the pump chamber in fluid communication with the fluid reservoir.

9 Claims, 4 Drawing Figures 4,661,097

METHOD FOR CLEARING A GAS BUBBLE FROM A POSITIVE DISPLACEMENT PUMP CONTAINED WITHIN A FLUID DISPENSING SYSTEM

BACKGROUND AND/OR ENVIRONMENT OF THE INVENTION

1. Field of the Invention

The invention relates to a method and apparatus for clearing gas bubbles from the pumping chamber of a bellows or positive displacement pump. In particular, the invention relates to a method and apparatus for clearing gas bubbles from a fluid reservoir and from the pumping chamber of a single valve positive displacement pump. The invention has specific application to clearing gas bubbles from an implantable or external medication infusion pump.

2. Description of the Contemporary and/or Prior Art

With the acceptance of both external and implantable infusion devices, researchers have been attempting to develop a pump which satisfies the strict performance requirements imposed on those devices. Research indicates that the positive displacement pump, such as a bellows pump, appears to be the most attractive type of pump for infusion devices. However, if even small gas bubbles enter into the pumping chamber of a bellows or positive displacement pump, the amount of fluid delivered per stroke (the stroke volume) will decrease. A significant gas bubble entering such a pump will stop the pumping of an incompressible liquid altogether, because the gas bubble can expand and/or compress before sufficient pressure is generated to open the inlet and/or the outlet valve(s).

Prior art references attempt to solve this problem by providing a filter means which prevents gas bubbles from entering the chamber. U.S. Pat. No. 4,191,181, issued to Manfred Franetzkion, on Mar. 4, 1981, attempts to solve this problem by using a wick like member composed of lightly packed glasslike fibers which have sufficient capillary forces to prevent gas from entering the fine channels. Similarly, U.S. Pat. No. 4,360,019, issued to Portner et al, attempts to solve this problem by using a looped tube that terminates a short distance from the side of the straight portion of the tube. This distance is smaller than the diameter of air bubbles, thus blocking their entry into the tube.

However, the prior art does not teach a method or apparatus for removing a gas bubble once it has found its way into the pumping chamber.

SUMMARY OF THE INVENTION

This invention relates to a U.S. patent application No. 4,594,058 entitled "Single Valve Diaphragm Pump with Decreased Sensitivity to Ambient Conditions", invented by R. E. Fischell and filed of even date herewith, which describes a single valve positive displacement pump. The pump contains a variable volume pumping chamber, an outlet valve and an inlet filter. Although the inlet filter provides resistance to fluid flow, it also allows fluid to flow in two directions, into and out of the pumping chamber. The present inventors recognized that such a pump could be freed from gas bubbles by applying a vacuum or negative pressure to the inlet filter, thereby drawing gas bubbles from the pumping chamber.

The present invention relates to a method and apparatus for removing gas bubbles from such a one-valve positive displacement pump and its associated fluid dispensing system. The preferred embodiment is used in association with an implantable infusion pump having a self-sealing septum in fluid communication with a fluid container, and a one-valve positive displacement pump in fluid communication with said fluid container via a filter which allows two-way fluid flow.

The present invention comprises the steps of: (1) inserting a non-coring hypodermic needle through a self-sealing septum on the outer surface of the implanted infusion device, thereby allowing the hypodermic needle to be in fluid communication with the fluid container located within said implantable infusion device and to be in fluid communication with the pumping chamber of a one-valve positive displacement pump contained within said implanted device; (2) drawing fluid from said fluid container and from said pumping chamber by applying a vacuum to said hypodermic needle; and, (3) refilling said infusion device by injecting a liquid from an external source through said hypodermic needle into said fluid container and said pumping chamber.

It is, therefore, the object of this invention to provide a method and apparatus for clearing gas bubbles from a positive displacement pump, such as that described in the above-referenced co-pending U.S. application now U.S. Pat. No. 4,594,058. The application of this invention is, however, not limited to any particular environment.

It is the second object of the invention to provide a method and apparatus for removing fluid (possibly containing gas bubbles) from the fluid handling system and pumping chamber of an implantable infusion pump and for refilling the fluid handling system and the pumping chamber with a new liquid and/or medication. It is intended that this operation be performed while the implantable infusion pump is implanted within a patient.

The foregoing and other objects, features and advantages of the present invention will become more apparent in light of the detailed description of the best mode of carrying out the invention set forth hereafter, and illustrated in the accompanying drawings.

BRIEF DESCRIPTION OF THE DRAWINGS

In order that the present invention may be more fully understood, it will now be described by example, with reference to the accompanying drawings in which.

DESCRIPTION OF THE PREFERRED EMBODIMENT

The present invention provides a method and apparatus for removing fluid and bubbles from the reservoir and pumping chamber of infusion devices. The invented method has application to an implantable infusion device which has the following characteristics: (1) A non-coring hypodermic needle must be insertable through a septum and/or through a valve so as to be in fluid communication with the medication reservoir. (If a valve is used it must be operable so as to allow two-way fluid flow, such as the poppet valve described in U.S. Pat. No. 4,573,994 entitled "Refillable Medication Infusion Apparatus", invented by Robert E. Fischell and filed Dec. 7, 1981 (SN 327,818); and (2) the pump chamber must be in two-way fluid communication with the reservoir through an inlet flow. restricting means such as described in U.S. Pat. No. 4,594,058 entitled "Single Valve Diaphragm Pump with Decreased Sensitivity to Ambient Conditions" invented by Robert E. Fischell, filed at even date herewith.

Figure 1:
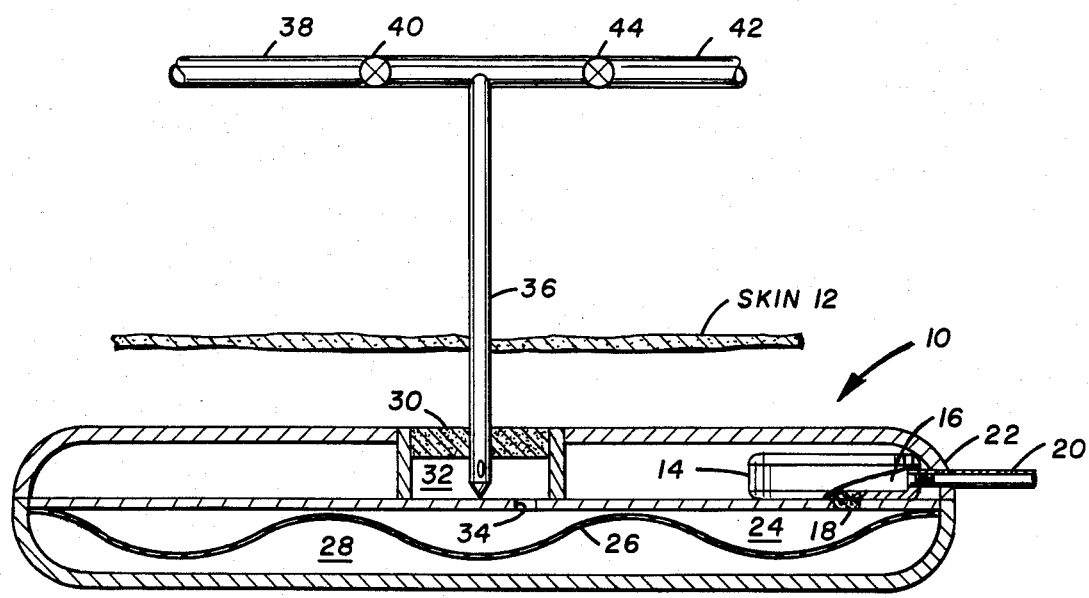
FIG. 1 illustrates the invented method and apparatus for removing gas bubbles from an implantable infusion system.

FIG. 1, illustrates a method and apparatus for removing fluid and gas bubbles trapped inside an infusion pump 10. The infusion pump 10 can be surgically implanted in a living body beneath the skin 12. The pump 14 (FIG. 1 does not show the pump mechanism), includes a pumping chamber 16 which has an inlet flow restricting means 18 and an exit port 20 that penetrates the outer surface of the infusion pump 10 and allows the delivery of medication to the appropriate point in the patient's body. The exit port contains an exit check valve 22 which will remain closed until a positive pressure above a certain level is produced in the pumping chamber 16. The inlet flow restricting means 18 could consist of an inlet filter or a flow restrictor which restricts the flow of fluid but enables fluid to slowly pass into pumping chamber 16 from reservoir 24, or from the pumping chamber 16 into the reservoir 24. The reservoir 24, shown in FIG. 1, is separated by a metallic diaphragm 26 from a vapor chamber 28 containing a pressurant such as Freon 113, some of which is in the liquid state with most of the volume being occupied by Freon vapor. When Freon 113 is used, the effect of vapor chamber 28 is to develop a negative pressure in reservoir 24. Alternatively, it is within the contemplation of the invention to use a reservoir held at positive, or ambient pressure, by the use of other liquid-vapor pressurant fluids. It is further contemplated that reservoirs which use a bellows chamber, or a bladder type container, or any similar medication container, can be practiced within the scope the present invention. The implantable pump device also comprises a self-sealing septum 30, which defines a portion of its outer boundary. Optionally, the implanted pump device can also contain antechamber 32 and an inlet valve 34. The inlet valve 34 is illustrated in FIG. 1 as an open portal since it can pass fluid in both directions. However, it should be noted that a hypodermic needle activated valve can be used in place of the open portal inlet valve 34. Furthermore, it should be noted that it is within the contemplation of the invention to apply the present invention to a septum which is in direct fluid communication with, or forms part of one wall of the reservoir or medication container.

If a bubble is trapped within the pump chamber 16, or if the physician desires to replace the fluid contained within the medication reservoir 24 and pump chamber 16, a non-coring hypodermic needle 36 can be inserted through the self-sealing septum 30 and into the antechamber volume 32. If a vacuum source is then connected to tube 38 and valve 40 is opened (with valve 44 closed), then liquid and/or gas bubbles contained in the antechamber 32, the reservoir 24, and the pump chamber 16 can be removed through the hypodermic needle 36 and drawn out tube 38. If the valve 40 is then closed and valve 44 is opened, liquid from a liquid source will enter through tube 42 and will fill the fluid-dispensing system, including: the pump chamber 16, the reservoir 24 and antechamber 32. After the bubble has been cleared, or the liquid replaced, hypodermic needle 36 can be removed and the fluid dispensing system will once more be operable. It should be noted that tubes 38 and 42, and valves 40 and 44, could be replaced by a syringe hypodermic needle or a similar means for drawing fluid through the hypodermic needle 36, or injecting liquid into the hypodermic needle 36.

Figure 2:
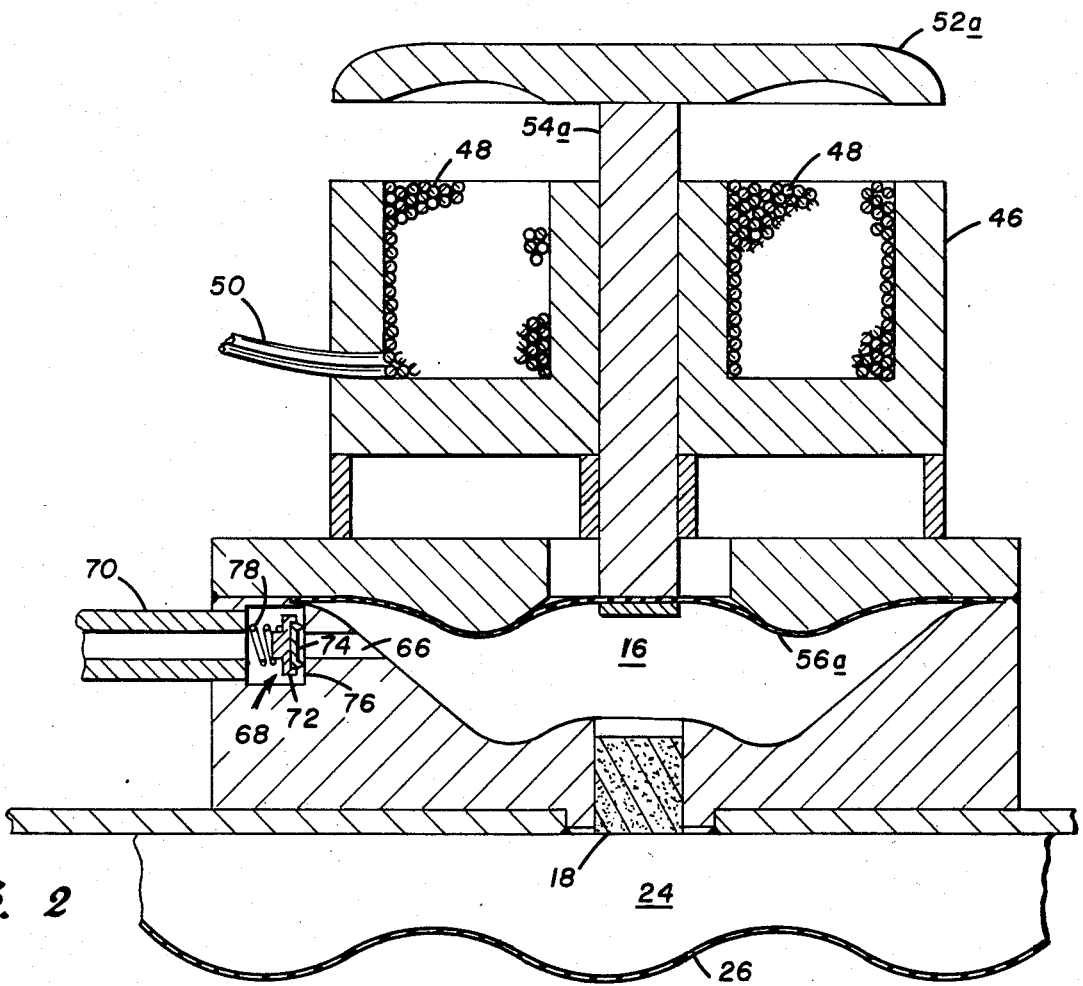
FIG. 2 illustrates a one-valve positive displacement pump in its rest position, as used in association with the present invention.
Figure 3:
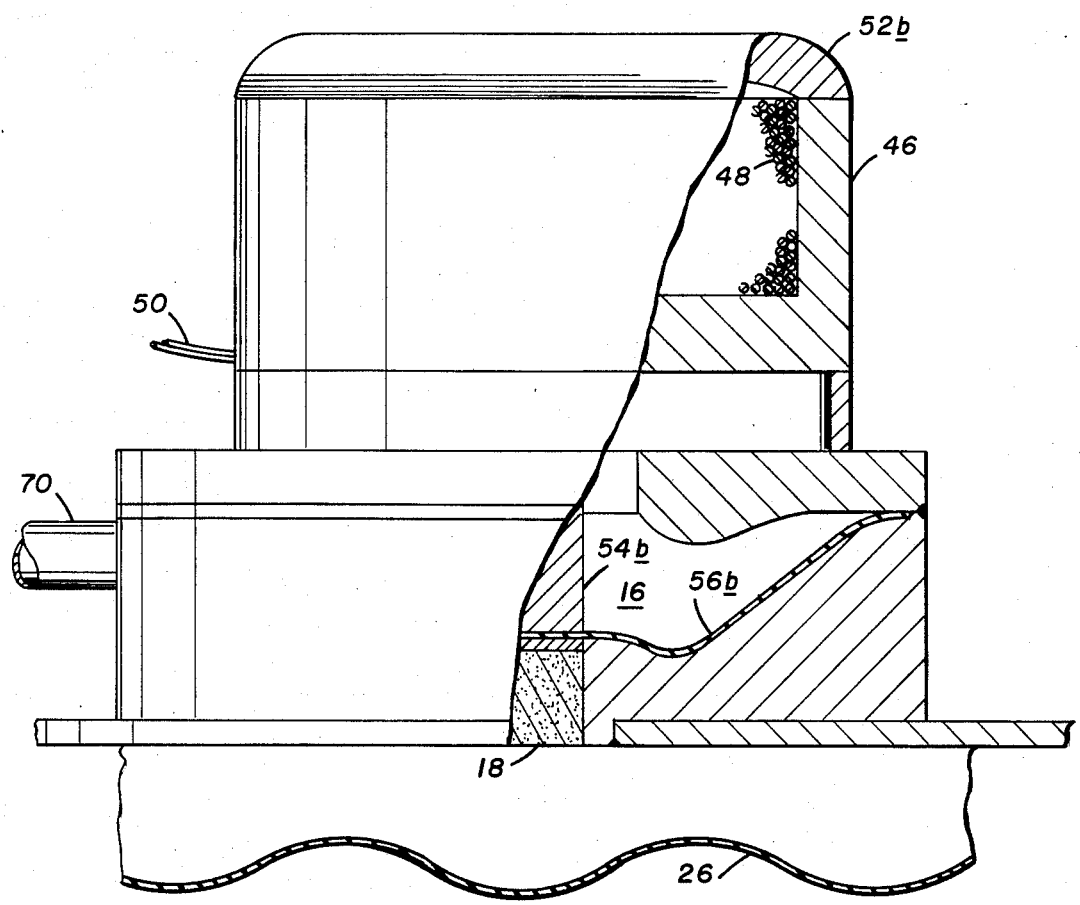
FIG. 3 illustrates a one-valve positive displacement pump in its fully actuated position as used in association with the present invention; and, FIG. 4 illustrates an inlet poppet valve used in association with the present invention, which enables a hypodermic needle, as taught by the present invention, to be in two-way fluid communication with the fluid handling system.

FIGS. 2 and 3 illustrate a single valve diaphragm pump which can be used with the present invention (FIG. 2 shows the pump in its rest position, FIG. 3 shows the pump in its actuation position). The pump is described in a U.S. Pat. No. 4,594,058 entitled "Single Valve Diaphragm Pump with Decreased Sensitivity to Ambient Conditions" by R. E. Fischell, and filed of even date herewith. A magnetic solenoid consisting of a magnetic core 46 has contained within its cylindrical structure solenoid coil 48 with lead-out wires 50. When a current pulse of electricity goes through the coil 48, via the lead wires 50, the magnetic core 46 is magnetized and the magnetic armature goes from its normal rest position 52a (see FIG. 2) to its actuation position 52b (see FIG. 3). In so doing, a cylinder attached at the center of the armature moves downward from its rest position 54a (see FIG. 2) to its fully actuated position 54b (see FIG. 3). This in turn results in a motion of the diaphragm from its normal or rest position 56a (see FIG. 2) to its full stroke (actuated) position 56b (see FIG. 3). After the solenoid coil is actuated with a pulse of electricity, the natural spring force of the diaphragm returns the diaphragm to its normal or rest position 56a thus causing the pump chamber volume 16 to be decreased on the actuated stroke and increased on the return stroke.

To describe the manner by which liquid is pumped, using the pump shown in FIGS. 2 and 3, let us begin with the diaphragm at its upward (rest) position 56a (see FIG. 2). At this point, the pump chamber 16 is at its maximum volume. Upon the actuation of the solenoid coil 48, the diaphragm is very rapidly (in approximately 1 ms) moved to a position 56b (see FIG. 3) thus decreasing the pump chamber volume to its smallest volume thus forcing liquid through the exit port chamber 66 (shown in Fig. 2), the exit valve 68, and the exit tube 70. The exit valve consists of a poppet having a metallic portion 72, and an elastometer portion 74 that is forced against a valve seat surface 76 by a valve spring 78.

A flow restricting means 18 (see FIG. 2) having a very high resistance to flow will allow a small amount of fluid (less than 10% of the stroke volume) to go through it into the reservoir on the down stroke. A filter can function as the flow restricting means 18 to provide a very high flow resistance which will only allow 1% or less liquid volume through it during the downward stroke of the diaphragm.

After the diaphragm has reached its fully extended position 56b (see FIG. 3), the natural spring force of the diaphragm will begin moving it upward towards position 56a (see FIG. 2). On the up (intake) stroke, liquid is drawn from reservoir 24 through the filter 18 into the pump chamber 16. The resistance of the filter 18 is sufficiently high so that the up stroke of the pump requires 0.1 second to several seconds depending on the pore size, length and area of the filter.

It must be noted that the invented method for removing a fluid and/or a fluid containing bubbles from the pump chamber will not be operable with the conventional pump design which uses a one-way inlet valve. The inlet valve would prevent the vacuum generated by the hypodermic needle 36 (see FIG. 1) from reaching the pump chamber 16. The present invented method is operable with a pump similar in design to that illustrated in FIGS. 2 and 3 and described in the above-referenced co-pending U.S. application. The pump uses an inlet flow restricting means, instead of an inlet valve, which could consist of a filter or any other flow restricting means such as a long tube of small diameter or a simple orifice with a very small hole.

Figure 4:
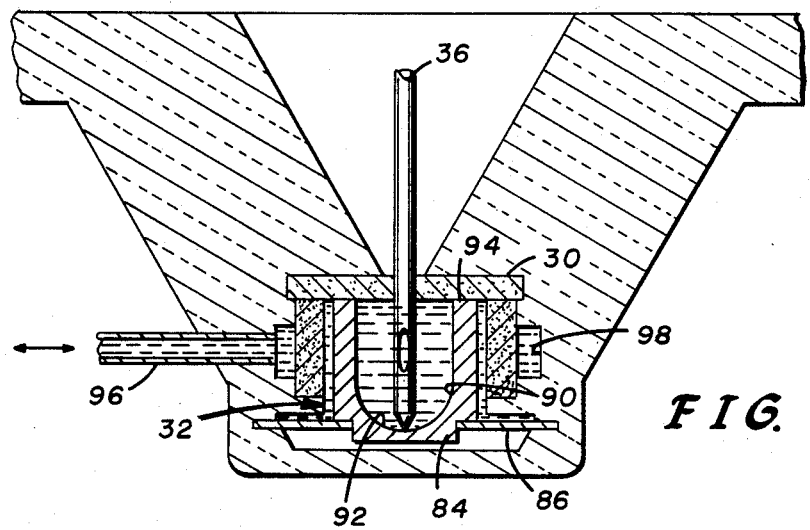

FIG. 4 illustrates an alternative valve design as compared to the open port valve 34 of FIG. 1 which provides a two-way fluid path from the antechamber 32 into the reservoir 24. One possible valve is described in U.S. Pat. No. 4,573,994 entitled "Refillable Medication Infusion Apparatus" invented by R. E. Fischell and filed Dec. 7, 1981. The hypodermic needle 36 is inserted through the self-sealing septum 30 (see FIG. 4) and enters antechamber 32. Positioned within antechamber 32 is a valve poppet 84 reciprocally mounted by a flexible diaphragm 86 fixedly secured to the walls of antechamber 32. The valve poppet 84 forms therein a recess 90 which is dimensioned to accept therein a hypodermic needle 36. When the needle 36 contacts the bottom 92 of recess 90, the valve poppet 84 then moves away from the septum 30 creating an opening between the septum 30 and the valve seal 94. When the valve seat 94 is open, the recess 90 is placed in communication with the balance of the antechamber 32 therefore permitting fluid introduced through the needle 36 to flow through into a conduit 96 through an annular fluid manifold 98. The conduit 96 is in communication with the medication reservoir, not illustrated. When the valve poppet 84 is in this downward or open position, hypodermic needle 36 can be used in accordance with the present invention to either draw fluid from the reservoir, via conduit 96, or inject fluid into the reservoir also via conduit 96. When the hypodermic needle 36 is withdrawn from the antechamber 32 the valve poppet 84 returns to its rest position thereby once again isolating the septum 30 from the medication reservoir, not illustrated. It should again be noted that the present invention could be utilized with any other septum antechamber valve combination which allows the hypodermic needle 36 to be in direct fluid communication with the reservoir.

Although the present invention has been described as having application with an external or implantable infusion pump, this procedure could be applicable in other environments. Obviously, many modifications and variations of the present invention are possible in light of the above teaching. It is therefore to be understood that within the scope of the appended claims the invention may be practiced otherwise than is specifically described.

What is claimed and desired to be secured by letters patent of the United States is:

1. A method for removing gas, gas bubbles or liquid from and infusion device, said method comprising the steps of:
    inserting a hypodermic needle through a self-sealing septum on the outer surface of said infusion device;
    providing bi-directional fluid communication between said hypodermic needle and a fluid container located within said infusion device;
    providing bi-directional fluid communication between said fluid container and a pump chamber of a single valve positive displacement pump; and,
    drawing fluid from said container and from said pump chamber by applying a vacuum to said hypodermic needle.

2. The method of claim 1 wherein said fluid container is in direct fluid communication with said pump chamber via an inlet flow restricting means.

3. The method of claim 1 wherein said fluid to be drawn from said fluid container and said pump chamber is a liquid.

4. The method of claim 1 wherein said fluid to be drawn from said fluid container and said pump chamber is a liquid and gas mixture.

5. The method of claim 1 wherein said fluid to be drawn from said fluid chamber and said pump chamber is a gas.

6. The method of claim 1 wherein said fluid to be drawn from said fluid container and said pump chamber is a liquid containing gas bubbles.

7. The method of claim 1, further comprising the step of injecting liquid from an external source through said hypodermic needle into said fluid container and said pump chamber.

8. The method of claim 1 wherein said fluid container comprises:
    an antechamber in fluid communication with said self-sealing septum;
    a reservoir; and,
    a reservoir port forming an outlet from said antechamber into said reservoir.

9. The method of claim 8, wherein said reservoir port includes a valve for selectively isolating said antechamber from said reservoir, said valve mechanically operable by placement of a portion of said hypodermic needle in a selected position.

* * * * *

UNITED STATES PATENT AND TRADEMARK OFFICE
CERTIFICATE OF CORRECTION

PATENT NO. : 4,661,097
DATED : April 28, 1987
INVENTOR(S) : Robert E. Fischell, Albert C. Sadilek and
William Swift It is certified that error appears in the above—identified patent and that said Letters Patent is hereby corrected as shown below:

In the claims:

Column 6, line 10, delete "and" and insert therefor -- an --.

Signed and Sealed this

Eighth Day of September, 1987

Attest:

DONALD J. QUIGG

Attesting Officer      Commissioner of Patents and Trademarks